United States Patent [19]

Chambaz et al.

[11] 4,438,480
[45] Mar. 20, 1984

[54] CAPACITIVE HYGROMETER

[75] Inventors: Bernard Chambaz, Seyssins; Gilles Delapierre, Seyssinet; Louis Destannes, Eybens, all of France

[73] Assignee: Commissariat a l'Energie Atomique, Paris, France

[21] Appl. No.: 281,603

[22] Filed: Jul. 9, 1981

[30] Foreign Application Priority Data

Jul. 9, 1980 [FR] France ................ 80 15263

[51] Int. Cl.³ ............................................. H01G 7/00
[52] U.S. Cl. .................... 361/278; 73/336.5; 361/286
[58] Field of Search ............... 361/286, 278, 304, 322; 73/336.5; 324/61 P; 338/35

[56] References Cited

U.S. PATENT DOCUMENTS

| | | | |
|---|---|---|---|
| 3,083,573 | 4/1963 | Shaw | 73/336.5 |
| 3,257,592 | 5/1966 | Maissel | 361/322 |
| 3,522,732 | 8/1970 | Bauer | 338/35 |
| 4,164,868 | 8/1979 | Suntola | 361/286 |
| 4,266,263 | 5/1981 | Haberl et al. | 361/278 |

Primary Examiner—B. A. Reynolds
Assistant Examiner—Alfred S. Keve
Attorney, Agent, or Firm—Michael N. Meller

[57] ABSTRACT

The present invention relates to a capacitive hygrometer comprising a capacitor (1) having a dielectric material (3), whose dielectric constant varies as a function of the quantity of water absorbed. It has on one of its conductive faces numerous fissures bringing the dielectric material into direct contact with the atmosphere whose degree of humidity is to be measured. However, the electrical continuity of the fissured conductive face is maintained. Application to the measurement of the degree of humidity of the air.

7 Claims, 3 Drawing Figures

CAPACITIVE HYGROMETER

BACKGROUND OF THE INVENTION

The present invention relates to a hygrometer functioning by means of a capacitive method, as well as to a process for producing this hygrometer.

A known means for measuring the humidity of the air consists of using a capacitor, whose dielectric absorbs a quantity of water which is a function of the relative humidity of the air and measuring the dielectric constant thereof.

For such an instrument to function correctly, at least one of the electrodes of the capacitor must be permeable to water, have a low electrical resistance and be relatively insensitive to corrosion.

In existing sensors, the compromise between these three requirements is generally brought about by the use of a vacuum-deposited ultra-thin gold coating (approx. 100 Å). Although the first two conditions are generally satisfactorily fulfilled (good electrical conductivity of the gold and good permeability because the coating is very thin) such capacitors have a poor corrosion resistance. Thus, a gold thickness of 100 Å can be relatively rapidly destroyed by pollutants, particularly sulphur-based pollutants ($SO_2$, $H_2SO_4$) and the life of the instrument is reduced.

A conventional means for solving this problem consists of protecting the gold coating by adding filters, e.g. in the form of the sheet of cellophane, However, this unfortunately has the effect of increasing the sensor response time and therefore reducing its sensitivity.

BRIEF SUMMARY OF THE INVENTION

The present invention relates to a capacitive hygrometer having both a good response time and a good corrosion resistance.

According to the main feature of the invention, the hygrometer is of the type constituted by a capacitor having a dielectric material whose dielectric constant varies as a function of the quantity of water absorbed, conductive faces of the capacitor being connected to means for measuring the dielectric constant and has on one of its conductive faces and in the dielectric numerous fissures bringing the dielectric material into direct contact with the atmosphere, whose relative humidity is to be measured. However, the electrical continuity of the fissured conductive face is maintained.

Due to the presence of these fissures, the dielectric is in direct contact with the atmosphere whose relative humidity is to be measured and is no longer separated therefrom by a thin metal coating to which is optionally added a filter. Thus, the operating speed of the hygrometer is significantly improved.

Moreover, the fissured electrode need no longer comprise a very thin metal coating, because it is scored to a significant extent. It can in fact be formed by one or more thicker layers of one or more materials with a greater resistance (e.g. a chromium layer), which makes it substantially insensitive to corrosion and increases the service life of the instrument.

BRIEF DESCRIPTION OF THE DRAWINGS

The invention is described in greater detail hereinafter relative to non-limitative embodiments and the attached drawings, wherein show.

DETAILED DESCRIPTION OF THE PREFERRED EMBODIMENTS

Figure 1:
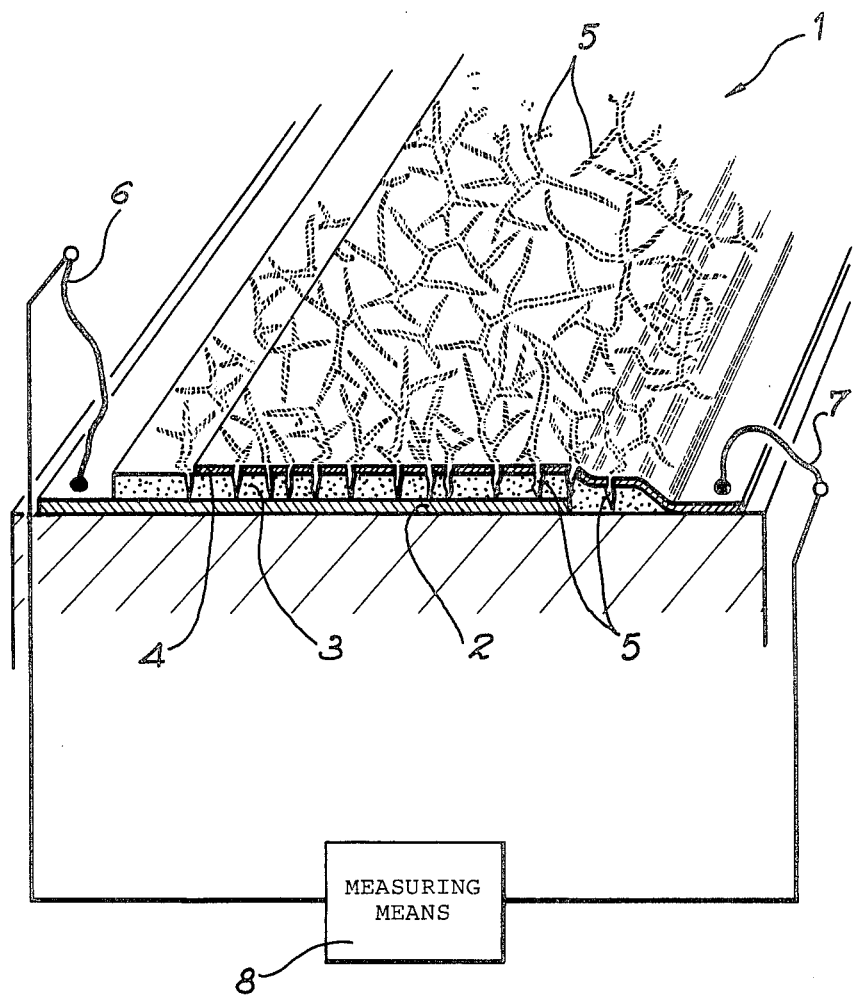
FIG. 1 a diagrammatic perspective view of a hygrometer according to the invention.

FIG. 1 shows capacitor 1 comprising a first continuous and unfissured electrode 2. This electrode carries dielectric 3, which can e.g. be a cellulose ester and then the other electrode 4. Electrode 4 and dielectric 3 are scored by numerous fissures 5. For reasons of clarity, the scale of the latter has deliberately been increased in the drawing, but in actual fact they can be microscopic fissures which are invisible to the naked eye. Finally, two conductor wires 6, 7, connected to electrodes 2, 4 respectively connect the capacitor to measuring means 8 permitting the determination of the dielectric constant thereof.

The fissured electrode 4 is constituted by a metal which is relatively insensitive to corrosion, such as chromium. In the presently described system, the humidity of the air does not have to traverse a thin metal coating and fissured electrode 4 may be impermeable and even very thick. Such hygrometers have been made with chromium thicknesses varying between 200 and 5000 Å, no significant difference in the response times having been detected. For the same reason, it is possible to further improve the corrosion resistance by adding to the chromium layer a precious metal layer, e.g. of platinum or gold, whilst further improving the life of the hygrometer.

The capacitor is produced by the deposition by evaporation onto the dielectric layer of a known metal so as to be tensionally stressed when deposited in the form of a thin coating and which contracts in such a way as to produce a large number of cracks. More specifically, a polymer layer, e.g. a cellulose ester serving as the dielectric is placed in an enclosure in which the vacuum has been formed. A metal is evaporated in the same enclosure and deposited on the dielectric, the experimental conditions being adjustable as a function of the desired thickness.

The first electrode is constituted by an anodically oxidized tantalum layer. The very thin tantalum oxide layer prevents any short-circuit between the two electrodes, even if there are holes in the polymer. It forms a very high capacitance in series with that of the polymer and consequently in no way reduces the sensitivity of the sensor.

Part of the first electrode is protected from oxidation for forming contacts. The polymer can be deposited by immersion in a solution, followed by drying.

The standard polymer used is cellulose acetate butyrate, but a good sensitivity level has been obtained with other polymers, such as polyimides or plexiglass.

The metal layer which is tensionally stressed for various, not well known reasons, exerts considerable forces on the polymer. As the latter is not sufficiently rigid the metal layer fissures, leading to the fissuring of the polymer layer. This leads to a network of very numerous microscopic fissures, whose width is a fraction of a micrometer.

This network of fissures defines small islands or islets of metal on the surface of the capacitor, the dimensions of the latter being approximately a few micrometers. However, it has been experimentally observed that there are always a certain number of contact points between the various islets and that the electrical continuity of the fissured electrode 4 is maintained.

Figure 2:
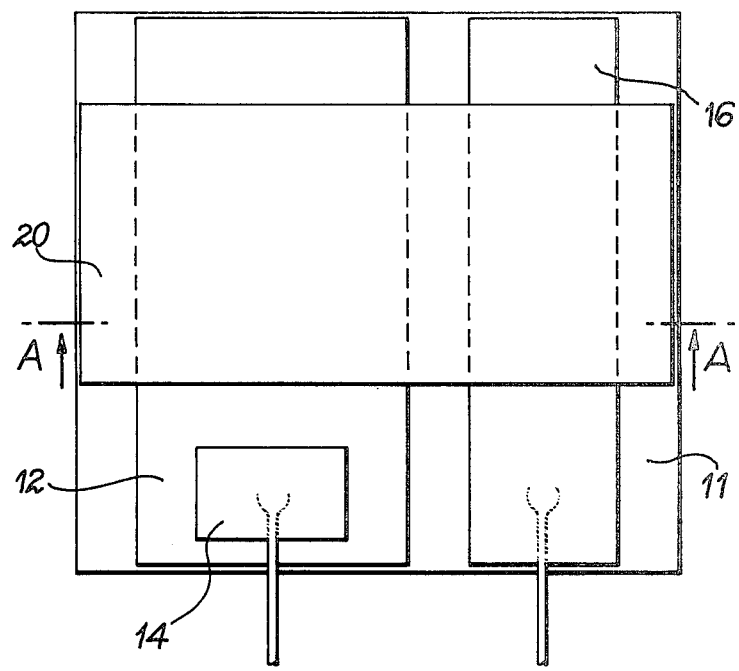
FIG. 2 a plan view illustrating a process for producing a hygrometer according to the invention.
Figure 3:
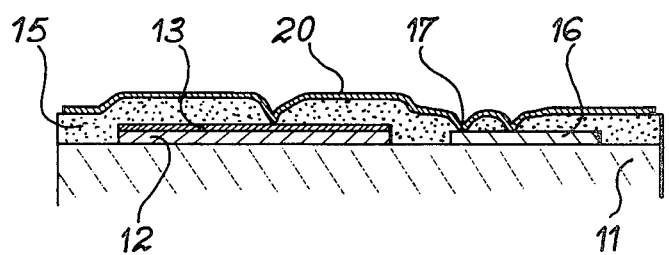
FIG. 3 a sectional view along line A—A of FIG. 2.

FIGS. 2 and 3 illustrate an embodiment of the production process for a hygrometer according to the invention.

On an insulating substrate 11 (e.g. of glass) is deposited a tantalum layer 12 forming the first electrode and is anodically oxidized so as to obtain a surface oxide layer 13. Contacting electrodes are then deposited, namely a first contacting electrode 14 on first electrode 12 and a second contacting electrode 16 on substrate 11 alongside the first tantalum electrode 12. The contacting electrodes can be of chromium, nickel or gold. In order to ensure the electrical contact between electrodes 14 and 12 it is either possible to protect electrode 12 against oxidation by means of a resin, or to perforate the oxide layer before making the bond or weld.

A polymer layer 15 is then deposited over the entire surface of substrate 11, so that it has a certain number of holes 17. In this connection it is advantageous to rapidly rotate the assembly by means of an apparatus of the type used for spreading photosensitive resins onto integrated circuits. The polymer is then left to dry and then a thick, porous chromium layer 20 is deposited thereon. If necessary, it is possible to adjust the capacitance of the capacitor by scraping the polymer and the chromium layer linked therewith. The holes 17 in the polymer layer ensure that the chromium provides the electrical contact with the contacting electrodes 16.

This process has made it possible to obtain 6×6 mm sensors produced in batchs of 49 with an efficiency of almost 100%.

Rapid calculations make it possible to estimate the gain in the response to time of the hygrometer according to the invention compared with a prior art hygrometer.

In a conventional hygrometer, the dielectric surface in contact with the humidity of the air (across a thin gold coating) is equal to the surface of the capacitor foils, whereas with the hygrometer according to the invention it is equal to the surface provided by means of the fissures. If d is the average distance between fissures, e the thickness of the polymer and if each islet is likened to a square and accepting that each fissure completely scores the dielectric, the ratio between the surfaces in contact with the atmosphere of a conventional sensor and of the hygrometer according to the invention is:

$$(d^2/4 \, ed)$$

Values of $e \simeq d \simeq 2$ μm have been obtained with the sensors produced. The surface in contact with the atmosphere is consequently multiplied by 4 for a same volume of dielectric material and for a same surface area of the capacitor foils. In fact, the tests which have been performed indicate an even greater gain for the response time. This shows that a fissured dielectric according to the invention allows water to penetrate much more easily than a dielectric which is merely covered by a very thin metal coating, as in the prior art hygrometers.

Thus, the hygrometer according to the invention offers numerous advantages. It is sensitive to the relative humidity of the air with a low response time. Moreover, it is relatively insensitive to corrosion because the fissured electrode no longer has to be very thin to permit the passage of the atmospheric humidity. In fact, it can have a significant thickness, which increases its life, as well as that of the hygrometer. In addition, the fissures have a very limited width (approximately 1000 to 2000 Å) and the generally larger atmospheric dust particles cannot penetrate them. This also contributes to the long service life of the instrument.

Finally, it is obvious that the capacitive sensor according to the invention can have applications other than hygrometric measurements. It is merely necessary to use as the dielectric layer a material whose dielectric constant varies as a function of the magnitude to be measured.

What is claimed is:

1. A capacitive hygrometer of the type constituted by a capacitor having a dielectric material between two conductive faces with said dielectric material having a dielectric constant which varies as a function of the quantity of water absorbed, said conductive faces being connected to means for measuring the dielectric constant, where one of the conductive faces of the capacitor, as well as the dielectric material have numerous random fissures bringing the dielectric material into direct contact with the atmosphere the relative humidity of which is capable of being measured, while the electrical continuity of the fissured conductive face is maintained.

2. A capacitive hygrometer as in claim 1, wherein the dielectric material is a cellulose ester.

3. A capacitive hygrometer as in claim 1 wherein the fissured conductive face is constituted by a conductive material which is relatively insensitive to corrosion.

4. A capacitive hygrometer as in claim 3, wherein the material forming the fissured conductive base is chromium.

5. A capacitive hygrometer as in claim 3 wherein the material forming the fissured conductive face is covered by a coating of a precious metal, selected from the group consisting of platinum and gold.

6. A capacitive hygrometer as in claim 1, wherein the other conductive face of the capacitor is formed by an anodically oxidized tantalum layer.

7. A capacitor constituted by a layer of dielectric material between two conductive faces, wherein one of the conductive faces, together with the dielectric material have numerous random fissures bringing the dielectric material into contact with the atmosphere in which the capacitor is placed each fissure scoring both the dielectric material and said conductive face with the electrical continuity of the fissured conductive face being maintained.

* * * * *